United States Patent [19]

Hideshima et al.

[11] Patent Number: 5,088,811
[45] Date of Patent: Feb. 18, 1992

[54] LASER BEAM SCANNING TYPE EYE FUNDUS OBSERVING DEVICE

[75] Inventors: Masayuki Hideshima; Shinji Wada; Akihiko Sekine, all of Tokyo, Japan

[73] Assignee: Kabushiki Kaisha TOPCON, Tokyo, Japan

[21] Appl. No.: 682,405

[22] Filed: Apr. 8, 1991

Related U.S. Application Data

[63] Continuation of Ser. No. 262,638, Oct. 26, 1988, abandoned.

[30] Foreign Application Priority Data

Oct. 26, 1987 [JP] Japan .................................. 62-270002

[51] Int. Cl.⁵ .................................................. A61B 3/10
[52] U.S. Cl. .................................... 351/221; 351/205
[58] Field of Search ........................ 351/205, 206, 221; 354/62; 128/303.1, 633; 606/4

[56] References Cited

U.S. PATENT DOCUMENTS 4,213,678  7/1980  Pomerantzeff ................ 351/221 X
4,877,321 10/1989  Ichihashi et al. ................ 351/221

Primary Examiner—Rodney B. Bovernick
Attorney, Agent, or Firm—Finnegan, Henderson, Farabow, Garrett & Dunner

[57] ABSTRACT

A laser beam scanning type eye fundus observing device has a scanning optical system for scanning and illuminating an eye fundus with a laser beam spot and an observation image of the eye fundus is built up in accordance with a reflecting light of the scanning laser beam from various portions of the eye fundus. The laser beam scanning type eye fundus observing device further has an output level regulator for automatically regulating an output level of an image signal in accordance with a light quantity information of the various portions of the eye fundus.

4 Claims, 5 Drawing Sheets

FIG.1
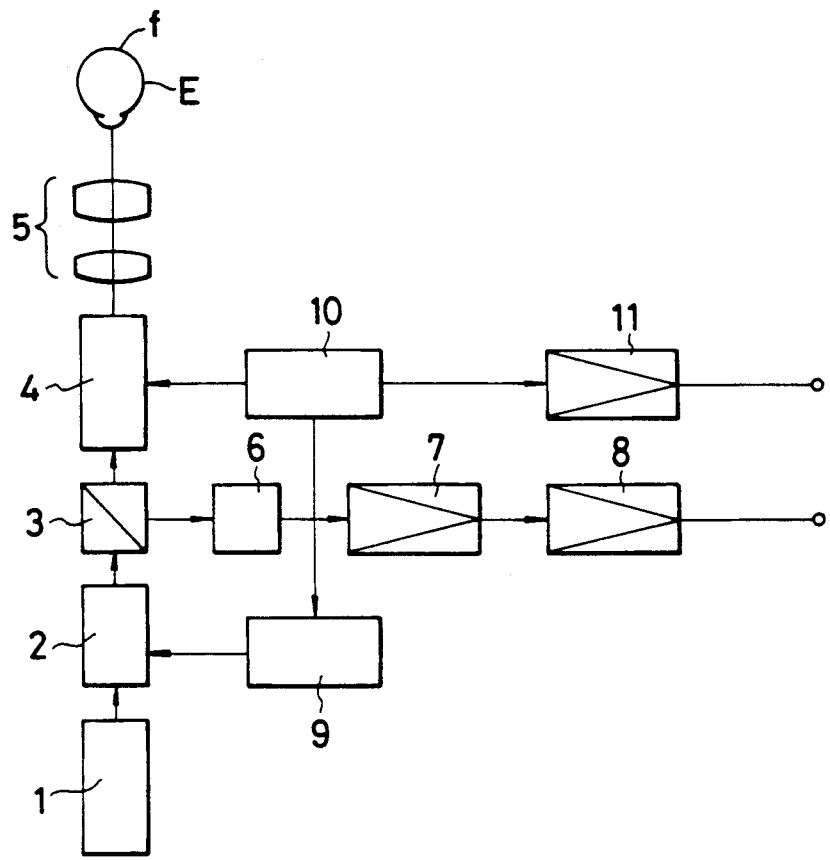
FIG.2
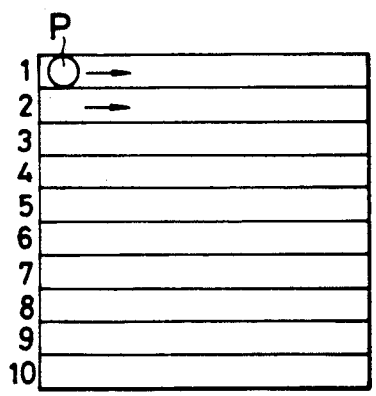
FIG.3

FIG. 4
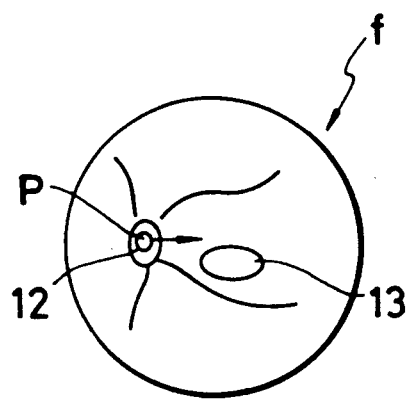
FIG. 5
FIG. 6
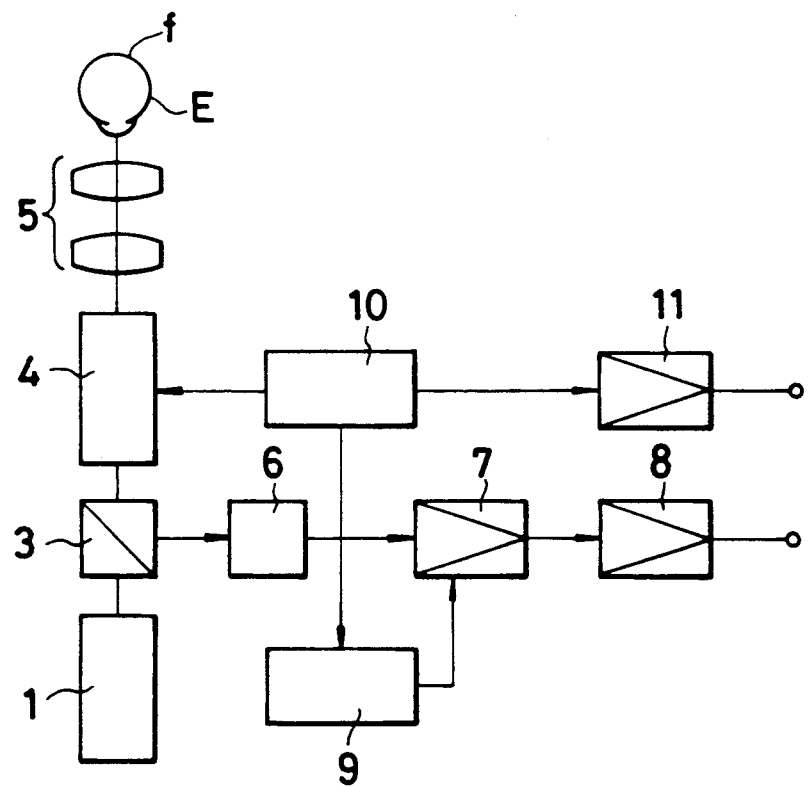

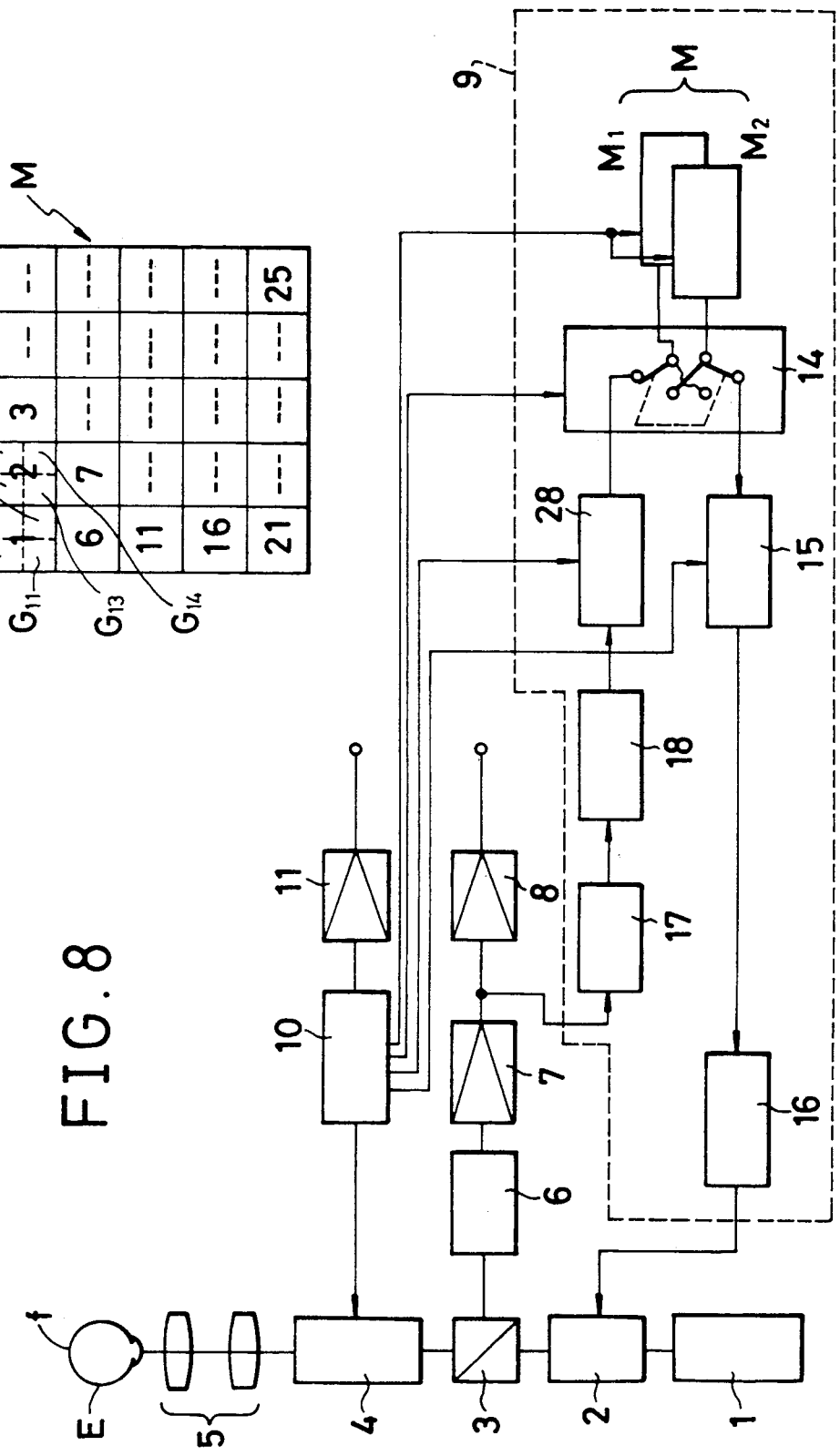

| OUTPUT OF 24 | OUTPUT OF 21 | OUTPUT OF 20 |
|---|---|---|
| $G(i-1, j-1)$ | $G(i-1, j)$ | $G(i-1, j+1)$ |
| OUTPUT OF 25 | OUTPUT OF 22 | OUTPUT OF 19 |
| $G(i, j-1)$ | $G(i, j)$ | $G(i, j+1)$ |
| OUTPUT OF 26 | OUTPUT OF 23 | INPUT |
| $G(i+1, j-1)$ | $G(i+1, j)$ | $G(i+1, j+1)$ |

LASER BEAM SCANNING TYPE EYE FUNDUS OBSERVING DEVICE

This application is a continuation of application Ser. No. 07/262,638, filed Oct. 26, 1988 now abandoned.

FIELD OF THE INVENTION

This invention relates to an improvement of a laser beam scanning type eye fundus observing device in which an eye fundus is scanned and illuminated with a laser beam spot and an observing image is built up based on a reflecting light of the scanning laser beam reflected by various portions of the eye fundus.

DESCRIPTION OF THE RELATED ART

Among conventional eye fundus observing devices, there are ones which have been used for photographing eye fundus, i.e., eye fundus cameras. However, it has been difficult for the conventional eye fundus cameras to take a photograph of an eye fundus clearly unless the observation illuminating light quantity, which has been used when observing an eye fundus, and the photograph illuminating light quantity, which has been used when photographing an eye fundus, were both large. When the illuminating light quantity was large, it often gave a dazzling feeling to a person under inspection and thus undesirable. Moreover, image irregularity of an eye fundus was produced on a photograph taken due to uneven illumination, etc. A further problem has arisen based on a large difference in reflectance between a papilla and a macula of the eye fundus. When an eye fundus image covering the pappila and the macula was taken in one sheet of photograph, the image of either pappila or macula had to be sacrificed on the photograph. In order to save both of them, special printing technique was required and thus troublesome.

In view of the above-mentioned problems, in recent time a laser beam scanning type eye fundus observing device has been and is still being developed, in which an eye fundus is scanned and illuminated by a laser beam spot and an observing image is built up based on a reflecting light of the scanning laser beam reflected by various portions of the eye fundus.

According to this laser beam scanning type eye fundus observing device, a laser beam is focused on various portions of an eye fundus, the eye fundus is succesively scanned and illuminated, and an observing image is obtained by a highly sensitive light receiving element. Accordingly, it has the advantages that the total incoming light quantity can be reduced and the eye fundus can be observing without giving a dazzling feeling to a person under inspection. However, there still remain some problem in how to prevent the occurrence of illumination irregularity, etc. Furthermore, with respect to the simultaneous observation of a pappila and a macula, the same difficulty as in the prior art till remains conventional eye fundus observing devices has been encountered in laser beam scanning type eye fundus observing devices.

OBJECT OF THE INVENTION

The present invention has been accomplished in view of the above-mentioned problems. It is therefore an object of the present invention to provide a laser beam scanning type eye fundus device, in which irregularity of an eye fundus image caused by illumination irregularity of a scanning optical system can be improved and various portions of the eye fundus having a large difference in reflectance can be observed simultaneously and clearly.

SUMMARY OF THE INVENTION

In order to achieve the above object, a laser beam scanning type eye fundus observing device includes an output level regulator for automatically regulating an output level of an image signal in accordance with light quantity information of various portions of an eye fundus (such as, for example, light quantity information obtained beforehand in correspondence with various portions of an eye fundus, and reflecting light information of a scanning laser beam reflected by various portions of an eye fundus).

Since a laser beam scanning type eye fundus observing device according to the present invention includes an output level regulator for automatically regulating output level of an image signal in accordance with a light quantity information coming from various portions of an eye fundus, the various portions of the eye fundus having a large difference in reflectance with respect one another can be observed simultaneously and clearly. In addition, irregularity of an eye fundus image caused by illumination irregularity can be improved.

BRIEF DESCRIPTION OF THE DRAWINGS

FIG. 1 is a schematic view of a laser beam scanning type eye fundus observing device according to a first embodiment of the present invention;

FIG. 2 is a schematic view showing one example of the scanning;

FIG. 3 is an illustration showing one example of an image element thereof;

FIG. 4 is an illustration showing one example of a memory corresponding to the image element;

FIG. 5 is a schematic view of an eye fundus;

FIG. 6 is an illustration showing a laser beam scanning type eye fundus observing device according to a second embodiment of the present invention;

FIG. 7 is an illustration showing another example of the memory of the embodiment illustrated in FIG. 4;

FIG. 8 is an illustration showing a laser beam scanning type eye fundus according to a third embodiment of the present invention;

DETAILED DESCRIPTION OF THE EMBODIMENTS

Figures 9, 10:
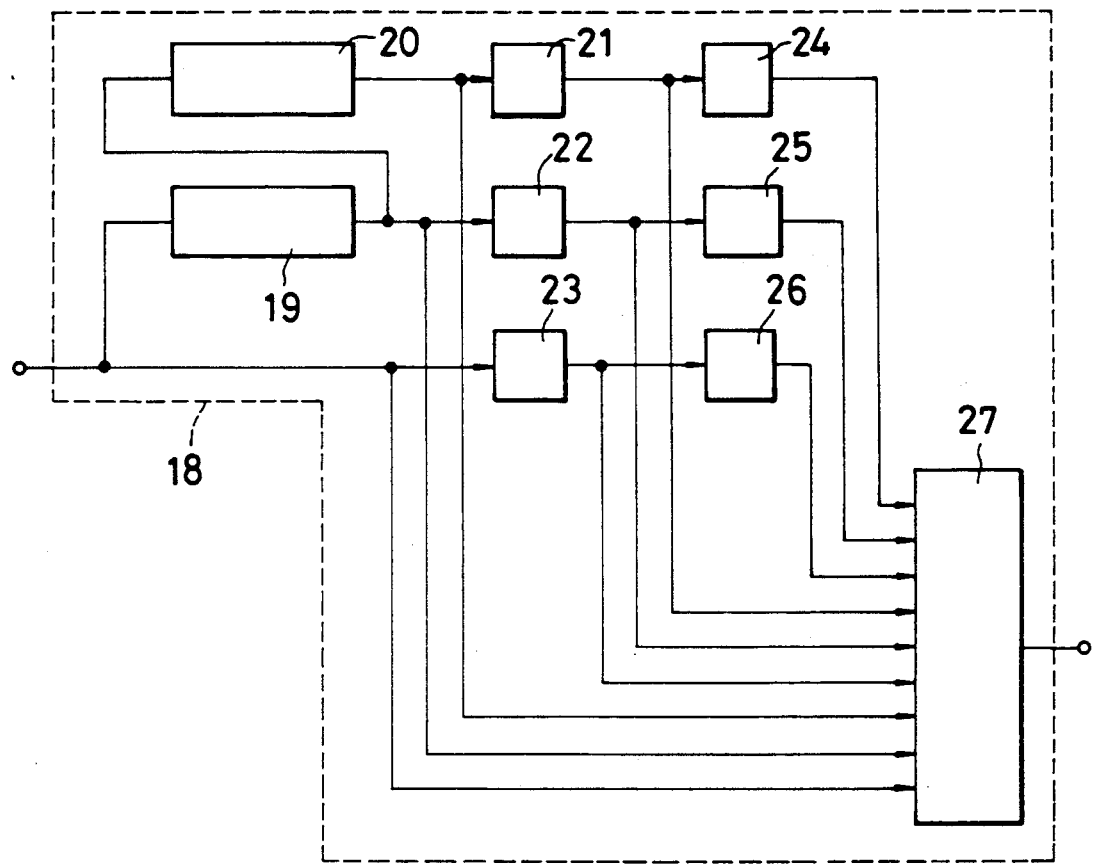
FIG. 9 is an illustration showing one example of a spatial filter of the embodiment illustrated in FIG. 8.
FIG. 10 is an illustration for explaining the correlation between the spatial filter and image elements.

Preferred embodiments of a laser beam scanning type eye fundus observing device according to the present invention will be described with reference to the accompanying drawings.

FIGS. 1 through 5 illustrate a laser beam scanning type eye fundus observing device according to a first embodiment of the present invention. In FIG. 1, 1 denotes a laser beam light source, 2 denotes a light modulator, 3 denotes a beam splitter, 4 denotes a two-dimensional scanner, 5 denotes an imaging lens and E denotes an eye to be inspected. The laser beam light source 1 used in this embodiment is for a visible radiation wavelength area. The laser beam light source 1 emits a laser beam of a visible radiation wavelength The laser beam emitted by the laser beam light source 1 is allowed to pass through the light modulator 2 and the beam splitter 3 and guided to the two-dimensional scanner. The two-dimensional scanner 4 deflects the outgoing laser beam, which then becomes a scanning laser beam by the two-dimensional scanner 4. The scanning laser beam is imaged on an eye fundus f by the imaging lens 5 as a laser beam spot P. Various portions of the eye fundus f are succesively scanned and illuminated by the laser beam spot P as shown in FIG. 2. In this embodiment, just for the convenience of explanation, the number of scanning lines is 10 and the aspect ratio of an image screen is 1:1.

The reflecting light of the scanning laser beam based on the scanning illumination is guided to a photoelectric transfer element 6 through the imaging lens 5, the two-dimensional scanner 4 and the beam splitter 3, and the reflecting light of the scanning laser beam corresponding to various portions of the eye fundus f is imaged on the photoelectric transfer element 6. The photoelectric transfer element 6 photoelectrically transfers the reflecting light of the scanning laser beam and outputs the same as photoelectric transfer signals corresponding to the various portions of the eye fundus f. The photoelectric transfer signals are amplified by an amplifier 7, then input into a signal processing circuit not shown through a buffer amplifier 8, and then built up as image signals. The signal processing circuit has an image memory. The image memory is arranged with a plurality of image elements G as a unit for signal processing. In this embodiment, for the convenience of explanation, the image elements G are arranged in a matrix shape consisting of 10 columns and 10 rows of image elements as shown in FIG. 3. The image signals are input into a television monitor. The television monitor displays an eye fundus image by succesively scanning the various image elements $G_1$ through $G_{100}$ in accordance with the image signals.

The light modulator 2 is controlled by a modulation signal generating circuit 9. The light modulator 2 has such a function as to modulate the intensity of the outgoing laser beam based on the modulation signal generating circuit 9. The modulation signal generating circuit 9 is input with a synchronous signal of a synchronous control circuit 10. The synchronous control circuit 10 has such a function as to control the modulation signal generating circuit 9 and the two-dimensional scanner 4. In addition, the synchronous control circuit 10 has such a function as to output a synchronous signal to the signal processing circuit through a buffer amplifier 11. The synchronous signal input into the signal processing circuit is used for succesively processing the photoelectric transfer signals to build up the image signals.

The modulation signal generating circuit 9 has a frame memory M as shown in FIG. 4. The frame memory M has address Nos. 1 through 100. Each of the addresses of the frame memory M is in correspondence with each of the address Nos. 1 through 100 of the various image elements G. The frame memory M stores in its address Nos. 1 through 100 reflectance information regarding the reflectance as an information of the quantity of reflected light from scanning beams of the various portions of the eye fundus corresponding to the various image elements G. The reflectance information stored in the addresses corresponding to the addresses of the image elements G which have been scanned is succesively read from the frame M. The modulation signal generating circuit 9 controls the light modulator 2 with reference to the reflectance information.

The light modulator 2 is controlled as such that when the laser beam spot P scans a portion of the eye fundus where the reflectance is relatively high (for example, portions of the papilla 12 of the eye fundus f as shown in FIG. 5), the intensity of the outgoing laser beam will become small, whereas when the laser beam spot P scans a portion of the eye fundus where the reflectance is relatively low (for example, macula 13), the intensity of the outgoing laser beam will become large.

By this, when the portions of the eye fundus where the reflectance is relatively high is scanned, the intensity of the laser beam spot is weakened and therefore, the intensity of the reflecting light of the scanning laser beam becomes proper. Thus, the output level of the image signal is not saturated. When the image is regenerated, the portions of the eye fundus where the reflectance is relatively high can be properly imaged on the image screen. On the other hand, when the portions of the eye fundus where the reflectance is relatively low are scanned, the laser beam spot is intensified and therefore, the intensity of the reflecting light of the scanning becomes proper. Thus, the output level of the image signal is not hidden by noise level. When the image is regenerated, the portions of the eye fundus where the reflectance is relatively low can be properly imaged on the image screen. Therefore, the light modulator 2 and the modulation signal generating circuit 9 function as an output level regulator for automatically regulating the output level of the image signal in accordance with the difference of the information of the reflecting light of the scanning laser beam from the various portions of the eye fundus.

FIG. 6 shows a laser beam scanning type eye fundus observing device according to a second embodiment of the present invention. In this second embodiment, instead of modulating the intensity of an outgoing laser beam by controlling the light modulator 2 by means of the modulation signal generating circuit 9, the amplification factor of the amplifier 7 is changed by the modulation signal generating circuit 9 as such that when the portions of the eye fundus where the reflectance is relatively high is scanned, the output level of a photoelectric transfer signal based on the reflecting light of the scanning laser beam will become low, whereas when the portions of the eye fundus where the reflectance is relatively low is scanned, the output level of a photoelectric transfer signal based on the reflecting light of the scanning laser beam will become high. Since the remaining constitution is almost the same as that of the first embodiment, identical component parts are denoted by identical reference numerals and detailed description thereof is omitted. In the above-mentioned two examples, if the spatial frequency required for modulation may be lower than that required for observation (for example, an image of such a tiny part as more or less a tiny blood vessel is desired to be left as it is but an image of a pappila or the like is desired to be treated), one address of the memory M can be corresponded to the adjacent plurality of image elements G. In this case, it may be designed as such that, as shown for example in FIG. 7, the address No. 1 of the memory M is corresponded to the images $G_1$, $G_2$, $G_{11}$ and $G_{12}$, the address No. 2 of the memory M is corresponded to the image elements $G_3$, $G_4$, $G_{13}$ and $G_{14}$, ... and the address No. 20 of the memory M is corresponded to the image elements $G_{89}$, $G_{90}$, $G_{99}$ and $G_{100}$ and the amplifier 7 is controlled by the information of reflectance factor which is stored in the address Nos. 1 through 20. It should be understood that the way of correspondence between the address Nos. of the memory M and the various image elements G is not limited to this. In the case only the portions of the eye fundus having a symmetry property are observed, the number of the address Nos. of the memory M, i.e., the memory capacity can be reduced. Furthermore, in the case the spatial frequency required for modulation is different for each portion of the eye fundus, the corresponding relation between the address Nos. of the memory M and the image elements G may be changed in accordance with the difference. The memory M shown in FIG. 7 may be used when the light modulator 2 is controlled.

In the first and the second embodiments described above, it is the premise that data (information of light quantity of the various portions of the eye fundus), which was obtained beforehand by calculation or other means, is written in the memory M beforehand and there is a corresponding relation of 1:1 between each portion of the eye fundus f and the image element G (memory M). For example, presuming that the information of the reflectance of the papilla 12 is stored in from address No. X to address No. Y of the memory M, if the corresponding relation between the pappila 12 and the image element G is broken, it occurs such an incidence as that the modulation signal generating circuit 9 controls the amplifier 7 or the light modulator 2 in accordance with the information of reflectance of other addresses and controls it by interpreting the reflectance as small although the reflectance is actually large because the portion scanned is the pappila 12. For example, in the case a left eye is observed by a pattern of a right eye, a portion having no relation with the papilla becomes dark because the position of the papilla is quite different. Therefore, the first and the second embodiments are effective only for eliminating a fixed pattern such as illumination irregularity of an optical system.

Further embodiments will be described, in which the control can be performed in accordance with the reflectance of each portion of the eye fundus without the premise of 1:1 corresponding relation between each portion of the eye fundus f and the image element G (memory M) as described.

FIGS. 8 through 10 show a laser beam scanning type eye fundus observing device according to the present invention. In FIG. 8, identical component parts to those of the first and the second embodiments are denoted by identical reference numerals. The frame memory M of the modulation signal generating circuit 9 comprises memories $M_1$ and $M_2$. The memories $M_1$ and $M_2$ store in each address thereof data of designation value $I_i(i=1$ through 100) for designating a certain intensity of light as an initial value. An input line and an output line of the memories $M_1$ and $M_2$ are connected to a memory selection circuit 14. The memory selection circuit 14 controls such that when data is being written in a desired address of one of the memories, data which is stored in an address corresponding to the desired address is read from the other memory according to a synchronous signal. When the writing into each address of one memory and the reading from each address of the other memory are completed for one frame, the synchronous control circuit 10 controls the memory selection circuit 14 as such that data is read from one memory and a reflectance information $R_i$ as will be described is written into each address of the other memory.

The data, which has been read from each address of either one of the memories $M_1$ and $M_2$, is converted to analog by a D/A converter 15 and then input into an inverse number circuit 16. The inverse number circuit 16 outputs a control signal having an output level $K/I_i$ multiplied by an inverse number as against the designation value $I_i$ according to the digital-to-analog conversion signal. The eye fundus f is scanned by a laser beam spot having a certain light intensity $K/I_i$ at the first scanning. The reflecting light of the scanning laser beam is photoelectrically transferred by the photoelectric transfer element 6, then amplified by the amplifier 7 and then input into the buffer amplifier 8 and a multiplying circuit 17. A photoelectric transfer signal passed through the buffer amplifier 8 is built into an image signal by a signal processing circuit not shown.

If the reflectance of each portion of the eye fundus is represented by $R_i$ ($i=1$ through 100), the intensity of the reflecting light of the scanning laser beam becomes $R_i \cdot K/I_i$. The multiplying circuit 7 has such a function as to obtain a reflectance information of each portion of the eye fundus. If a gain from the laser beam light source 1 to the amplifier 7 is represented by A and if it is selected that a constant K becomes $K=1/A$, the multiplying circuit 17 is input with a photoelectric signal having a value of $R_i/I_i$. If the product of the photoelectric transfer signal having a value of $R_i/I_i$ and the data having the designation value $I_i$ is obtained, only the signal for the reflectance information $R_i$ is extracted. The signal for the reflectance information $R_i$ is input in the spatial filter 18. The spatial filter 18 used in this embodiment is shown for example in FIG. 9.

In FIG. 9, 19 and 20 denote delay lines for delaying the signal transmittance for the time required for one horizontal scanning period, 21 through 26 denote delay lines for delaying the signal transmittance for a period of time required for scanning one image element, and 27 denotes an add circuit. The delay lines 19 through 26 and the add circuit 27 are connected with each other as shown in the figure. If the delay line 22 is corresponded with an image element $G(i,j)$ to which attention is paid, the add circuit 27 is input with reflectance information of adjacent image elements $G(i-1,j-1)$, $G(i-1,j)$, $G(i-1,j+1)$, $G(i-1,j)$, $G(i,j+1)$, $G(i+1,j-1)$, $G(i+1,j)$ and $G(i+1,j+1)$ shown in FIG. 10. The add circuit 27 obtains a reflectance information for the image element $G(i,j)$ by dividing the image number 9 by the reflectance information.

Such obtained reflectance information of each image element G is input into an A/D converter 28, then converted to a digital signal and then input into an address corresponding to an image element which is immediately above the left of the image element to which attention is paid. As a result, data, which is stored in each address of the other memory M, is rewritten into a reflectance information. By repeating this rewriting procedure per one frame, the reflectance information stored in each address of the memory is converged into a certain value. In this way, the density of the laser beam spot for scanning the eye fundus is properly controlled in correspondence with the reflectance information of each portion of the eye fundus, and the pappila 12 and the macula 13 can properly be displayed on an image screen. The spatial filter 18 may permit such a large image as that of the pappila 12 and macula 13 to pass but may not permit a smaller image (for example, image of blood vessel) to pass.

According to this embodiment, since the reflectance information includes the reflecting light quantity of the scanning laser beam based on the illumination irregularity of the scanning optical system, the irregularity of an eye fundus image caused by the illumination irregularity of the scanning optical system can be improved.

Figure 11:
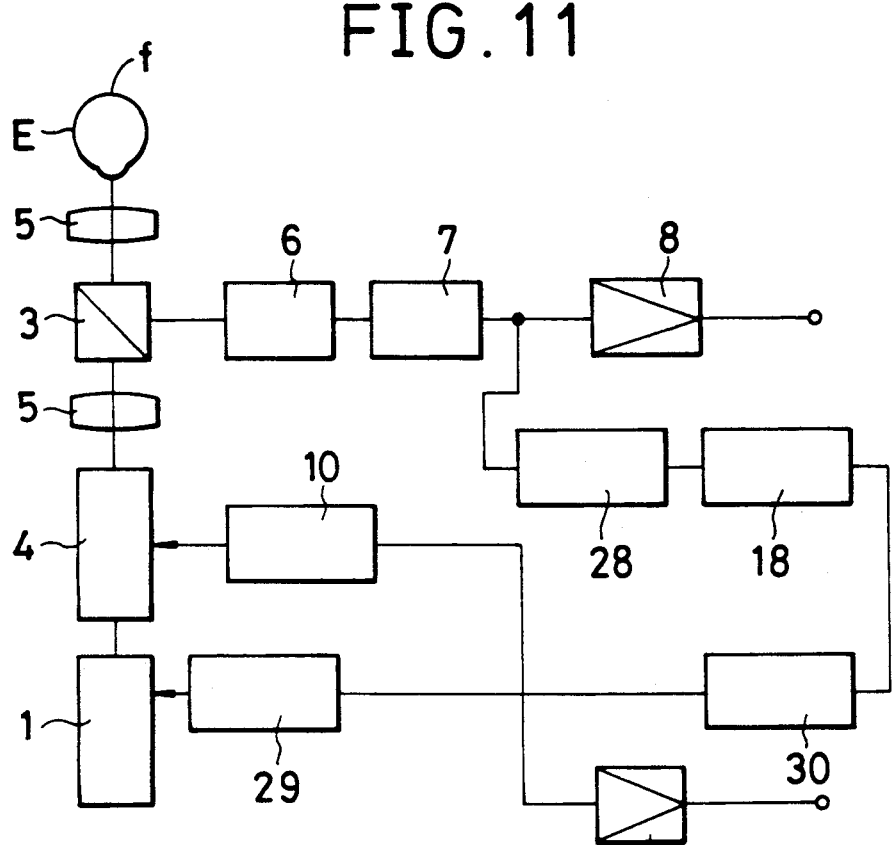
FIG. 11 is an illustration showing a laser beam scanning type eye fundus observing device according to a fourth embodiment of the present invention.
Figure 12:
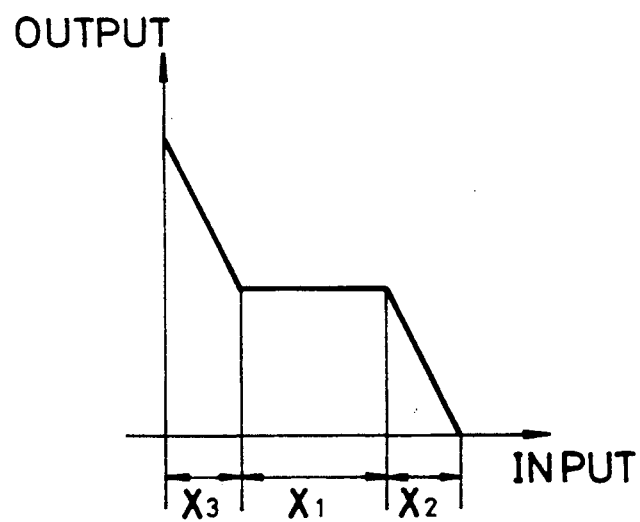
FIG. 12 is a graph showing the input and output characteristics of a broken line characteristic circuit of the embodiment illustrated in FIG. 11.

FIGS. 11 and 12 show a laser beam scanning type eye fundus observing device according to a fourth embodiment of the present invention. In this embodiment, the beam splitter 3 is placed between a pair of image lenses 5. And, a total reflecting light from the eye fundus f is guided to the photoelectric transfer element 6 so that the reflecting light quantity can be used effectively. Instead of the reverse number circuit 16 and the multiplication filter 17, a broken line characteristic circuit 28 is placed between the amplifier 7 and the spatial filter 18, and a laser driver 29 is controlled in accordance with the broken line characteristic shown in FIG. 2. In FIG. 2, $X_1$ denotes an intermediate gradation portion of the eye fundus portions, $X_2$ denotes a bright gradation portion of the eye fundus portions, and $X_3$ denotes a dark gradation portion of the eye fundus portions. When a photoelectric transfer signal corresponding to the intermediate gradation portion $X_1$ is input, the output power of the broken line characteristic circuit 28 is constant, whereas when a photoelectric transfer signal corresponding to the bright gradation portion $X_2$ is input, the output power of the broken line characteristic circuit 28 is reduced. Similarly, when a photoelectric transfer signal corresponding to the dark gradation portion $X_3$ is input, the output power of the broken line characteristic circuit 28 is increased. The output power of the broken line characteristic circuit 28 is input into a laser driver 29 through a one frame delay line 30. Controlled by the output power, the laser driver circuit 29 controls the laser beam light source 1 such that when the bright pappila 12 is scanned, the amplitude of the intensity of the laser beam becomes comparatively small, whereas when the dark macula 13 is scanned, it becomes comparatively large. The reason why the output power of the spatial filter 18, which is obtained before one frame, is used by using the one frame delay line is that since the spatial filter 18 is constituted by using data of the image element to which attention is paid and eight image elements therearound and to which attention is paid, information of an image element, which can be obtained timewise later than the image element to which attention is paid, is required. Since the time for obtaining a spatial filter of the image element, to which attention is paid, is available and the amplifier 7, the broken line characteristic circuit 28, the laser driver 29 and the laser beam light source 1 can also be considered as the delay elements, strictly to speak, it actually delayed by somewhat shorter time than one frame time.

According to the fourth embodiment, since the light intensity is adjusted by feeding back per each frame according to a fixed pattern instead of using the reflectance R of each portion of an eye fundus, the stability is improved.

What is claimed is:

1. A laser beam scanning type eye fundus observing device for generating a level-adjusted detected image signal from which can be constructed an observation image of an eye fundus viewable by an observer, comprising:

a scanning optical system having means for providing a laser light beam having a level of intensity, and means for scanning and illuminating the eye fundus with said laser light beam to cause a portion of said laser light beam to be reflected from the eye fundus;

means for generating a detected image signal in response to the intensity level of the portion of the laser light beam reflected from the eye fundus;

means for storing information representing the reflectances of various portions of the eye fundus, said information at least partially independent of the detected image signal; and an output level regulator for controlling the intensity level of the laser light beam of said scanning optical system in accordance with a stored information whereby said detected image signal becomes said level-adjusted detected image signal, wherein said output level regulator includes a light modulator, and a modulation signal generating circuit for controlling said light modulator so as to control the intensity level of the laser beam of said scanning optical system in accordance with said stored information.

2. A laser beam scanning type eye fundus observing device for generating a level-adjusted detected image signal from which can be constructed an observation image of an eye fundus viewable by an observer, comprising:

a scanning optical system having means for providing a laser light beam having a level of intensity, and means for scanning and illuminating the eye fundus with said laser light beam to cause a portion of said laser light beam to be reflected from the eye fundus;

means for generating a detected image signal in response to the intensity level of the portion of the laser light beam reflected from the eye fundus;

means for storing information corresponding to various portions of the eye fundus, said information at least partially independent of the detected image signal; and an output level regulator for controlling the level of said detected image signal in accordance with a stored information whereby said detected image signal becomes said level-adjusted detected image signal, wherein said means for generating a detected image signal includes a photoelectric transfer element for photoelectrically transferring the portion of the laser beam reflected from the eye fundus to provide said detected image signal, and an amplifier for amplifying said detected image signal, and wherein said output level regulator includes a modulation signal generating circuit for controlling the amplification factor of said amplifier to control the level of said detected image signal in accordance with said stored information.

3. A laser beam scanning type eye fundus observing device for generating a level-adjusted detected image signal from which can be constructed an observation image of an eye fundus viewable by an observer, comprising:

a scanning optical system having means for providing a laser light beam having a level of intensity, and means for scanning and illuminating the eye fundus with said laser light beam to cause a portion of said laser light beam to be reflected from the eye fundus;

means for generating a detected image signal in response to the intensity level of the portion of the laser light beam reflected from the eye fundus;

means for storing information representing the reflectances of various portions of the eye fundus, said information at least partially independent of the detected image signal; and an output level regulator for controlling the intensity level of the laser light beam of said scanning optical system in accordance with a stored information whereby said detected image signal becomes said level-adjusted detected image signal, wherein said output level regulator includes means for updating said information in accordance with the intensity level of the portion of the laser beam reflected from the eye fundus, and means for automatically controlling the intensity level of the laser light beam of said scanning optical system in accordance with said stored information.

4. A laser beam scanning type eye fundus observing device for generating a level-adjusted detected image signal from which can be constructed an observation image of an eye fundus viewable by an observer, comprising:

a scanning optical system having means for providing a laser light beam having a level of intensity, and means for scanning and illuminating the eye fundus with said laser light beam to cause a portion of said laser light beam to be reflected from the eye fundus;

means for generating a detected image signal in response to the intensity level of the portion of the laser light beam reflected from the eye fundus;

means for storing information representing the reflectances of various portions of the eye fundus, said information at least partially independent of the detected image signal; and an output level regulator for controlling the level of said detected image signal in accordance with a stored information whereby said detected image signal becomes said level-adjusted detected image signal, wherein said output level regulator includes means for updating said information in accordance with the intensity level of the portion of the laser beam reflected from the eye fundus, and means for automatically controlling the intensity level of said output laser light beam of said scanning optical system in accordance with said stored information.

* * * * *